US006869793B2

(12) United States Patent
Cardosa et al.

(10) Patent No.: US 6,869,793 B2
(45) Date of Patent: Mar. 22, 2005

(54) RECOMBINANT MVA VIRUS EXPRESSING DENGUE VIRUS ANTIGENS, AND THE USE THEREOF IN VACCINES

(75) Inventors: Mary Jane Cardosa, Sarawak (MY); Gerd Sutter, Munich (DE); Volker Erfle, Munich (DE)

(73) Assignee: Bavarian Nordic Research Institute, Glostrup (DK)

(*) Notice: Subject to any disclaimer, the term of this patent is extended or adjusted under 35 U.S.C. 154(b) by 0 days.

(21) Appl. No.: 09/147,919

(22) PCT Filed: Sep. 23, 1997

(86) PCT No.: PCT/EP97/05214

§ 371 (c)(1), (2), (4) Date: Mar. 23, 1999

(87) PCT Pub. No.: WO98/13500

PCT Pub. Date: Apr. 2, 1999

(65) Prior Publication Data

US 2003/0082205 A1 May 1, 2003

(30) Foreign Application Priority Data

Sep. 24, 1996 (DK) .............................................. 1035/96

(51) Int. Cl.[7] ...................... C12N 15/85; C12N 15/863; C12N 5/10

(52) U.S. Cl. .................. 435/320.1; 435/325; 435/69.3; 536/23.72

(58) Field of Search .......................... 435/235.1, 320.1, 435/69.1, 69.3, 325; 536/23.72; 514/44; 424/199.1

(56) References Cited

U.S. PATENT DOCUMENTS

| | | | | | |
|---|---|---|---|---|---|
| 5,185,146 | A | * | 2/1993 | Altenburger ............... | 425/69.1 |
| 5,369,025 | A | * | 11/1994 | Nazerian et al. ......... | 435/235.1 |
| 5,494,671 | A | * | 2/1996 | Lai et al. ................. | 424/218.1 |
| 5,514,375 | A | * | 5/1996 | Paoletti et al. ........... | 424/199.1 |
| 5,744,141 | A | * | 4/1998 | Paoletti et al. ........... | 424/199.1 |
| 6,074,865 | A | * | 6/2000 | Kelly et al. .............. | 253/235.1 |
| 6,440,422 | B1 | | 8/2002 | Sutter et al. | |

FOREIGN PATENT DOCUMENTS

| | | | | |
|---|---|---|---|---|
| WO | WO 90 01946 A | | 3/1990 | |
| WO | 92/15672 | * | 9/1992 | ............ C12N/7/00 |
| WO | 92/16636 | * | 10/1992 | ........... C12N/15/86 |

OTHER PUBLICATIONS

Sutter et al (FEBS LETT. 371:9–12), 1995.*

Wyatt et al (Virology 210:202–5), 1995.*

Sutter et al (PNAS 89:10847–10851), 1992.*

Moss (Seminars in Immunology 2:317–327), 1990.*

Hayes et al (Pediatric infectious disease journal 11(4):311–7, abstract only cited), 1992.*

Bancroft.(Puerto Rico health sciences journal 6(11):23–6, abstract only cited), 1987.*

Monath et al. Flaviviruses. In: Fields Virology, third edition, ed. B. N. Fields et al. pp. 997–1004, 1996.*

Zhang et al. BBRC 200(1): 95–101, Apr. 1994.*

Selby et al (Journal of Virology 71: 7827–7831, Oct. 1997).*

Hirsch, V.M. et al., "Limited Virus Replication Following SIV Challenge of Macaques Immunized With Attenuated MVA Vaccinia Expressing SIVsm env and gag–pol" *Vaccines 95 Modern Approaches to New Vaccines* 95:195–200 (1995).

Sutter, G. and Moss, B., "Novel Vaccinia Vector Derived From the Host Range Restricted and Highly Attenuated MVA Strain of Vaccinia Virus" *Developments in Biological Standardization* 84:195–200 (1995).

Yamshchikov, V.F. et al., "Generation of Long Flavivirus Expression Cassettes by in vivo Recombination and Transient Dominant Selection" *Gene* 149:193–201 (1994).

* cited by examiner

*Primary Examiner*—Mary E. Mosher

(74) *Attorney, Agent, or Firm*—Antoinette F. Konski; Bingham McCutchen LLP

(57) ABSTRACT

Recombinant MVA viruses containing and/or capable of expressing dengue virus antigens and the use of such recombinant MVA for vaccination.

5 Claims, No Drawings

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 33 base pairs (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(iii) HYPOTHETICAL: YES (iv) ANTI-SENSE: NO (xi) SEQUENCE DESCRIPTION: SEQ ID NO: 1:

CAGCAGGGTA CCCTCATCGT ACAGGACGTT CTC                              33

(2) INFORMATION FOR SEQ ID NO: 2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 2:

CAGCAGCCCG GGTATTCGAT GATTATTTTT AACAAAATAA CA                    42

(2) INFORMATION FOR SEQ ID NO: 3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(iii) HYPOTHETICAL: YES (iv) ANTI-SENSE: NO (xi) SEQUENCE DESCRIPTION: SEQ ID NO: 3:

CAGCAGCTGC AGGAATCATC CATTCCACTG AATAGC                           36

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 4:

CAGCAGGCAT GCCGACGAAC AAGGAACTGT AGCAGA                           36

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

-continued (xi) SEQUENCE DESCRIPTION: SEQ ID NO: 5:

CAGCAGGTCG ACCCCGACCG CCTTACTGCC GCC            33

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 6:

GGGGGGCTGC AGATGGTAGC GACCGGCGCT CAG            33

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 7:

CAGCAGCCCG GGATGGCAGC AATCCTGGCA TACACC         36

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 8:

CAGCAGCCCG GGTCACTGTA GTTTGTCCAT CCTCAGCCT      39

RECOMBINANT MVA VIRUS EXPRESSING DENGUE VIRUS ANTIGENS, AND THE USE THEREOF IN VACCINES

The present invention relates to recombinant vaccinia viruses derived from the modified vaccinia virus Ankara (MVA) encoding and capable of expressing dengue virus antigens, and the use of such recombinant MVA viruses encoding dengue virus antigens in vaccines.

BACKGROUND OF THE INVENTION

Dengue viruses are divided into four antigenically related serotypes, called dengue virus serotypes 1, 2, 3, and 4. Complete or partial nucleotide sequences of the dengue 1, 2, 3, and 4 type virus have been published (Chamber, T. J., Hahn, C. S., Galler, R. And Rice, C. M. 1990. Annu. Rev. Microbiol., 44, 649, Zhao et al., 1986, Virology 155, 77–88).

Dengue virus, with its four serotypes Den-1 to Den-4, is the most important member of the Flavivirus genus with respect to infections of humans producing diseases that range from flu-like symptoms to severe or fatal illness, dengue haemorrhagic fever with shock syndrome. Dengue outbreaks continue to be a major public health problem in densely populated areas of the tropical and subtropical regions, where mosquito vectors are abundant. Therefore, there is a substantial need for the development of prophylactic vaccines. Previous efforts to prepare live candidate dengue vaccines were mainly based on classical attenuation of dengue virus by serial passage in animals or in cultured cells of non-natural hosts. However, this approach has not been consistently successful in producing attenuated vaccine strains. Available data indicate that recovery and protective immunity after dengue virus infection are correlated to the development of high titres of virus neutralising antibodies. However, this immunity is homotypic mediating resistance to the same virus serotype only. Moreover, individuals immune to one dengue virus serotype may be even at higher risk of developing severe dengue illness if reinfected with another serotype. To overcome these problems an ideal vaccine should therefore induce solid immunity against all four dengue virus serotypes.

The flavivirus genome consists of a single-stranded positive sense RNA molecule. The single encoded open reading frame (ORF) is translated into a polypeptide which is cleaved co- and post-translationally into at least 11 proteins. The order of proteins encoded in the ORF is 5'-C-preM(M)-E-NS1-NS2A-NS2B-NS3-NS4A-NS4B-NS5-3' (Venugopal, K., and Gould, E. A., 1994, Vaccine, Vol. 12, No. 11).

Previous results from vaccine trials in animal models indicated that immune responses to structural preM and E proteins, or non-structural NS1 proteins were fully protective against a lethal challenge with homotypic dengue virus (Zhao et al. 1987 J. Virol. 61:4019; Bray et al. 1989 J. Virol. 63:2853; Falgout et al. 1990 J. Virol. 64:4356; Fonseca et al. 1994 Vaccine 12:279; Srivastava et al. 1995 Vaccine 13:1251).

The preM protein (18–19 kDa) is a precursor of the structural protein M, which is formed by cleavage and removal of the N-terminal (pre) segment, by a process presumed to be linked to maturation of the envelope glycoprotein and the development of virus infectivity.

The E glycoprotein (53–54 kDa) is an outer structural protein of the dengue virus. It exhibits a number of biological activities including receptor binding and membrane fusion, and is the target for neutralising antibodies and T-helper cells. The E protein is a typical membrane glycoprotein with a C-terminal that spans the membrane.

The non-structural protein NS1 (39–41 kDa) is also modified by glycosylation. It is derived from the ORF by N-terminal signalase cleavage and C-terminal cleavage involving a protease. NS1 may be involved in the assembly and release of virions. It is found on the cell surface and in the culture medium of infected cells. During the course of infection, NS1 protein evokes a strong antibody response which protects the host against challenge with flaviviruses, presumably through a complement mediated pathway, although recently is has been suggested that other mechanisms such as antibody-dependent cell cytotoxicity may also be responsible (Venugopal, K., & Gould, E. A., 1994, Vaccine, Vol. 12, No. 11).

Knowledge about the molecular biology of flaviviruses rapidly increased during the last decade, and led to the application of recombinant techniques for the production of new vaccine candidates. These approaches have included $E.$ $coli$ fusion proteins, baculo virus produced recombinant proteins, and live recombinant vaccinia viruses. Notably, the vaccinia approaches have given promising results. In mice, total protection against lethal challenge with dengue virus has been achieved after immunisation with recombinant vaccinia viruses expressing structural and/or non-structural genes of dengue virus (J Gen Virol, 1988, 69: 2102–7).

There is still the need for the development of a safe and an effective vaccine with a major goal in the prevention, and perhaps the treatment, of DF and DHF/DSS in humans. As mentioned above only approaches using recombinant vaccinia virus have given so far promising results. However, occurrence of rare adverse reactions to smallpox vaccination and the increased susceptibility of immunodeficient individuals has made further attenuation and improved safety a priority for human vaccines based on recombinant vaccinia virus.

Modified vaccinia virus Ankara (MVA), is a host range restricted and highly attenuated vaccinia virus strain, which is unable to multiply in human and most other mammalian cell lines tested. But since viral gene expression is unimpaired in non-permissive cells recombinant MVA viruses may be used as exceptionally safe and efficient expression vectors.

The modified vaccinia virus Ankara (MVA) has been generated by long-term serial passages of the Ankara strain of vaccinia virus (CVA) on chicken embryo fibroblasts (for review see Mayr, A., Hochstein-Mintzel, V. and Stickl, H. (1975) Infection 3, 6–14; Swiss Patent No. 568, 392). The MVA virus was deposited in compliance with the requirements of the Budapest Treaty at CNCM (Institut Pasteur, Collection Nationale de Cultures de Microorganisms, 25, rue du Docteur Roux, 75724 Paris Cedex 15) on Dec. 15, 1987 under Depositary No. I-721. The MVA virus has been analyzed to determine alterations in the genome relative to the wild type CVA strain. Six major deletions of genomic DNA compared with the wild type CVA (deletion I, II, III, IV, V, and VI) totalling 31,000 base pairs have been identified (Meyer, H., Sutter, G. and Mayr A. (1991) J. Gen. Virol. 72, 1031–1038). MVA is further distinguished by its great attenuation, that is to say by diminished virulence or infectivity while maintaining good immunogenicity. When tested in a variety of animal models, MVA was proven to be avirulent even in immunosuppressed animals. More importantly, the excellent properties of the MVA strain have been demonstrated in extensive clinical trials (Mayr et al., Zbl. Bakt. Hyg. I, Abt. Org. B 167, 375–390 (1987), Stickl et al., Dtsch. med. Wschr. 99, 2386–2392 (1974)). During these studies in over 120,000 humans, including high risk patients, no side effects were associated with the use of MVA vaccine. MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. (1992) Proc. Natl. Acad. Sci. USA 89,10847–10851). Recently, novel vaccinia vector systems were established on the basis of MVA, having foreign DNA sequences inserted at the site of deletion III within the MVA genome (Sutter, G. and Moss, B. (1995) Dev. Biol. Stand. Basel, Karger 84,195–200). Another approach used, except less successfully (Scheiflinger et al., 1996, Arch Virol 141, 663–669) the tk gene within the MVA genome (U.S. Pat. No. 5,185,146).

According to the present invention, DNA sequences (genes) which code for dengue antigens are introduced, with the aid of DNA recombination techniques, into the genome of MVA. When the DNA sequence encoding the dengue antigen is integrated at a site in the viral DNA which is non-essential for the life cycle of the virus, e.g. one of the above mentioned deletions, the newly produced recombinant MVA will be infectious, that is to say able to infect foreign cells and it will express the integrated DNA sequence. The recombinant MVA according to the invention will be useful as extremely safe live vaccines for the treatment or prophylactics of infectious diseases.

OBJECTS OF THE INVENTION

It is thus an object of the present invention to provide a recombinant MVA virus expressing dengue virus antigens, which can serve as an efficient and exceptionally safe dengue virus vaccine.

It is a further object of the present invention to provide vaccines for the immunisation of a living animal body, including a human, infected with dengue virus, and for the prevention of dengue virus infection.

SUMMARY OF THE INVENTION

The present invention thus, inter alia, comprises the following, alone or in combination:

A recombinant MVA containing and capable of expressing one or more DNA sequences encoding dengue virus antigens;

a recombinant MVA as above containing and capable of expressing DNA sequences encoding antigens from all four dengue virus serotypes (type 1, 2, 3 and 4);

a recombinant MVA as above wherein the dengue virus antigens is selected from preM, E and/or NS1 antigens;

a recombinant MVA as above wherein the DNA sequences are inserted at the site of naturally occurring deletions within the MVA genome;

a recombinant MVA as above wherein the DNA sequences encoding antigen is under transcriptional control of the vaccinia virus early/late promoter P7.5;

a vaccine containing at least one recombinant MVA as above, and a pharmaceutically acceptable carrier or diluent;

a vaccine as above containing a recombinant MVA encoding a dengue virus type 1 antigen; a recombinant MVA encoding a dengue virus type 2 antigen; a recombinant MVA encoding a dengue virus type 3 antigen, and/or a recombinant MVA encoding a dengue virus type 4 antigen, and a pharmaceutically acceptable carrier or diluent;

a method for the treatment or prevention of dengue virus infection comprising administering to a living animal body, including a human, in need thereof a therapeutically effective amount of a recombinant MVA as above, or a vaccine as above.

a vaccine comprising as a first component a recombinant MVA carrying and capable of expressing T7-RNA polymerase and as further components one or more recombinant DNA vectors each carrying at least one dengue virus antigen under transcriptional control of a T7 RNA polymerase promoter; and a method for the treatment or prevention of a dengue virus infection comprising inoculating a living animal body, including a human, in need thereof with the first and further components of the vaccine as above either simultaneously or with a timelag but using the same inoculation site.

THE PRESENT INVENTION

The present invention relates to recombinant MVA which contain at least one DNA sequence which codes for a dengue virus antigen and vaccines containing such viruses in a physiologically acceptable form. The invention also relates to methods for the preparation of such recombinant MVA and vaccines, and to the use of these vaccines for the prophylactics or treatment of infections caused by dengue virus.

Modified vaccinia virus Ankara (MVA), is a host range restricted and highly attenuated vaccinia virus strain, which is unable to multiply in human and most other mammalian cell lines tested. But since viral gene expression is unimpaired in non-permissive cells recombinant MVA viruses may be used as exceptionally safe and efficient expression vectors. Therefor recombinant MVA according to the invention contain and are capable of expressing one or more DNA sequences encoding dengue virus antigens.

In one embodiment, according to the present invention, DNA sequences (genes) which code for dengue antigens capable of eliciting immune responses to dengue virus are provided. Such sequences are optionally introduced, with the aid of DNA recombination techniques, into the genome of viral expression systems including for example the MVA vector. When the DNA sequence encoding the dengue antigen or antigenic epitope is integrated at a site in the viral DNA which is non-essential for the life cycle of the virus, e.g. one of the above mentioned deletions, the newly produced recombinant MVA will be infectious, that is to say able to infect foreign cells and it will express the integrated DNA sequence. The recombinant viruses and the recombinant MVA according to the invention will be useful as extremely safe live vaccines for the treatment or prophylactics of dengue infection.

The recombinant MVA vaccinia viruses can be prepared as set out hereinafter.

For homologous recombination of the wild type MVA DNA with a heterologous nucleotide acid sequence in a virus infected cell a DNA-constructs containing sequences adjacent to the left and the right side of a naturally occurring deletion, e.g. deletion II or III, within the MVA genome (Altenburger, W., Suter, C. P. and Altenburger J. (1989) Arch. Virol. 105, 15–27) were constructed, e.g. as described in Example 4.

The DNA sequence encoding antigenic epitopes is inserted between the sequences flanking the naturally occurring deletion, e.g. as described in Example 5 to 8.

A DNA-construct, according to the invention, which contains a DNA-sequence which codes for a dengue antigen flanked by MVA DNA sequences adjacent to a naturally occurring deletion, e.g. deletion II or III, within the MVA genome, is introduced into cells infected with MVA, to allow homologous recombination. The DNA-construct to be inserted can be linear or circular. A circular DNA is preferred, especially a plasmid.

For the expression of a DNA sequence encoding antigenic epitopes, it is necessary for regulatory sequences, which are required for the transcription of the DNA sequence, to be present on the DNA. Such regulatory sequences (called promoters) are known to those skilled in the art, and includes for example those of the vaccinia 11 kDa gene as are described in EPA 198, 328, those of the 7.5 kDa gene (EPA 110, 385) or the synthetic promoter sP (Sutter et al., Vaccine, 1994, 12:1032)

The DNA-construct can be introduced into the MVA infected cells by transfection, e.g. by means of calcium phosphate precipitation (Graham et al., Virol. 52,456–467 (1973); Wigler et al., Cell 777–785 (1979) by means of electroporation (Neumann et al., EMBO J. 1, 841–845 (1982)), by micro-injection (Graessmann et al., Meth. Enzymology 101, 482–492 (1983)), by means of liposomes (Straubinger et al., Methods in Enzymology 101, 512–527 (1983)), by means of spheroplasts (Schaffner, Proc. Natl. Acad. Sci. USA 77, 2163–2167 (1980)) or by other methods known to those skilled in the art. Transfection by means of calcium phosphate precipitation is preferred.

Once the DNA-construct has been introduced into the eukaryotic cell and the foreign DNA has recombined with the viral DNA, it is possible to isolate the desired recombinant vaccinia virus in a manner known per se, preferably with the aid of a marker (compare Nakano et al., Proc. Natl. Acad. Sci. USA 79, 1593–1596 (1982), Franke et al., Mol. Cell. Biol. 1918–1924 (1985), Chakrabarti et al., Mol. Cell. Biol. 3403–3409 (1985), Fathi et al., Virology 97–105 (1986)).

The recombinant MVA according to the invention can also carry a marker gene. Said marker genes facilitates the isolation of a recombinant virus using techniques well known to anyone skilled in the art. Such marker genes are preferably selected from the group consisting of marker genes which codes for proteins such as β-galactosidase, neomycin, alcohol dehydrogenase, luciferase, puromycin, hypoxanthine phosphoribosyl transferase (HPRT), hygromycin, secreted alkaline phosphatase or green and blue fluorescent proteins.

The present invention therefore also relates to recombinant MVA which contains at least one DNA sequence which codes for dengue virus antigens and relates further to vaccines containing such viruses in a physiologically acceptable form.

In one embodiment, the recombinant MVA according to the invention contain and is capable of expressing antigens from all dengue virus type 1, type 2, type 3 and type 4.

In a preferred embodiment of the invention the dengue virus antigen is selected from preM, E and/or NS1 antigens originating from dengue virus type 1, 2, 3 or 4.

The invention also relates to vaccines comprising recombinant MVA according to the invention containing and capable of expressing one or more DNA sequences encoding dengue virus antigens.

In one embodiment, the vaccine according to the invention comprises a recombinant MVA encoding dengue virus type 1 antigen; a recombinant MVA encoding dengue virus type 2 antigen; a recombinant MVA encoding dengue virus type 3 antigen; and/or a recombinant MVA encoding dengue virus type 4 antigen.

In a further embodiment of the invention recombinant MVA encoding T7 RNA polymerase is used in combination with at least one DNA vectors carrying DNA sequences encoding dengue antigens under transcriptional control of a T7 RNA polymerase promoter.

According to this embodiment, a coding sequence of a given dengue antigen (e.g. preM, E, and/or NS1) are cloned under control of a T7 RNA polymerase promoter preferably in a plasmid vector and the resulting DNA construct is amplified and purified using standard laboratory procedures. Secondly, the vector DNA is inoculated simultaneously or with appropriate timelags together with MVA-T7pol . An appropriate timelag allows a cell to takeup the inoculated DNA vector, before MVA infection takes place. The mode of administration, the dose and the number of administrations can be optimised by those skilled in the art in a known manner. At the site of inoculation the recombinant gene of interest is expressed transiently in cells containing both the vector DNA and MVA-T7pol and the corresponding antigen is presented to the host immune system stimulating an antigen-specific immune response. This protocol using the vaccinia vector MVA-T7pol represents a promising novel approach to nucleic acid vaccination allowing efficient transient expression of a given antigen, but avoiding the potential risk of constitutive gene expression.

The detailed figures and examples which follow are intended to contribute to a better understanding of the present invention. However, it is not intended to give the impression that the invention is confined to the subject-matter of the examples.

EXAMPLE 1

Growing of the MVA Virus

The MVA virus is a highly attenuated vaccinia virus derived from the vaccinia virus strain Ankara (CVA) by long-term serial passages on primary chicken embryo fibroblast (CEF) cultures. For a general review of the history of the production, the properties and the use of MVA strain, reference may be made to the summary published by Mayr et al. in Infection 3, 6–14 (1975). Due to the attenuation in CEF, the MVA virus replicates to high titres in this avain host cell. In mammalian cells, however, MVA is severely growth restricted, and typical plaque formation by the virus is not detectable. Therefore, MVA virus was grown on CEF cells. To prepare CEF cells, 11-days old embryos were isolated from incubated chicken eggs, the extremities are removed, and the embryos are minced and dissociated in a solution composed of 0.25% trypsin at 37° C. for 20 minutes. The resulting cell suspension was filtered and cells were sedimented by centrifugation at 2000 rpm in a Sorvall RC-3B centrifuge at room temperature for 5 minutes, resuspended in 10 volumes of medium A (MEM Eagle, for example obtainable from Life Technologies GmbH, Eggenstein, Germany), and sedimented again by centrifugation at 2000 rpm in a Sorvall RC-3B centrifuge at room temperature for 5 minutes. The cell pellet was reconstituted in medium A containing 10% fetal calf serum (FCS), penicillin (100 units/ml), streptomycin (100 mg/ml) and 2 mM glutamine to obtain a cell suspension containing 500 000 cells/ml. CEF cells obtained in this way were spread on cell culture dishes. They were left to grow in medium A in a 6% $CO_2$ atmosphere with 95% humidity at 37° C. for 1–2 days, depending on the desired cell density, and were used for infection either directly or after one further cell passage. A detailed description of the preparation of primary cultures can be found in the book by R. I. Freshney, "Culture of animal cell", Alan R. Liss Verlag, New York (1983) Chapter 11, page 99 et seq. MVA viruses were used for infection as follows. CEF cells were cultured in 175 cm² cell culture bottles. At 90–100% confluence, the medium was removed and the cells were incubated for one hour with an MVA virus suspension (0.01 infectious units (IU) per cell, 0.02 ml/cm²) in medium A. Then more medium A was added (0.2 ml/cm²) and the bottles were incubated at 37° C. for 2–3 days (until about 90% of the cells show cytopathogenic effect). Crude virus stocks were prepared by scraping cell monolayers into the medium and pelleting the cell material by centrifugation at 3000 rpm in a Sorvall RC-3B centrifuge at 4° C. for 5 minutes. The crude virus preparation was stored at −20° C. before further processing (e.g. virus purification).

EXAMPLE 2

Cloning of MVA Virus

To generate homogeneous stock virus preparations MVA virus obtained from Prof. Anton Mayr was cloned by limiting dilution during three consecutive passages in CEF cultured on 96-well tissue culture plates. The MVA clone F6 was selected and amplified in CEF to obtain working stocks of virus that served as starting material for the generation of recombinant MVA viruses described in this patent application as well as for the generation of recombinant MVA viruses described previously (Sutter & Moss (1992) Proc. Natl. Acad. Sci. USA 89, 10847–10851; Sutter, et al.,(1994) Vaccine 12, 1032–1040; Hirsch, et al., (1996) J. Virol. 70, 3741–3752).

EXAMPLE 3

Purification of the Viruses

The purification steps undertaken to obtain a virus preparation which was as pure as possible and free from components specific to the host cell were similar to those described by (joklik, Virology 18, 9–18 (1962)). Crude virus stocks which had been stored at −20° C. were thawed and suspended once in PBS (10–20 times the volume of the sediment), and the suspension was centrifuged as above. The new sediment was suspended in 10 times the volume of Tris buffer 1 (10 mM Tris-HCl pH 9.0), and the suspension was briefly treated with ultrasound (Labsonic L, B. Braun Biotech International, Melsungen Germany; 2×10 seconds at 60 watts and room temperature) in order to further disintegrate cell debris and to liberate the virus particles from the cellular material. The cell nuclei and the larger cell debris were removed in the subsequent brief centrifugation of the suspension (Sorvall GSA rotor obtainable from DuPont Co., D-6353 Bad Nauheim, FRG; 3 minutes at 3000 rpm and 10° C.). The sediment was once again suspended in Tris buffer 1, treated with ultrasound and centrifuged, as described above. The collected supernatants containing the free virus particles were combined and layered over a cushion of 10 ml of 36% sucrose in 10 mM Tris-HCl, pH 9.0, and centrifuged in a Beckman SW 27/SW 28 rotor for 80 minutes with 13,500 rpm at 4° C. The supernatant was discarded, and the sediment containing the virus particles was taken up in 10 ml of 1 mM Tris-HCl, pH 9.0, homogenised by brief treatment with ultrasound (2×10 seconds at room temperature, apparatus as described above), and applied to a 20–40% sucrose gradient (sucrose in 1 mM Tris-HCl, pH 9.0) for further purification. The gradient was centrifuged in Beckmann SW41 rotor at 13,000 rpm for 50 minutes at 4° C. After centrifugation, discrete bands containing virus particles were harvested by pipetting after aspirating volume above band. The obtained sucrose solution was diluted with three volumes PBS and the virus particles were sedimented again by centrifugation (Beckmann SW 27/28, 60 minutes at 13,500 rpm, 4° C.). The pellet, which now consisted mostly of pure virus particles, was resuspended in PBS and equilibrated to virus concentrations corresponding on average to $1-5\times10^9$ IU/ml. The purified virus stock solution was stored at −80° C. and used either directly or diluted with PBS for subsequent experiments.

EXAMPLE 4

Construction of Vector Plasmids

To allow the generation of recombinant MVA viruses novel vector plasmids were constructed. Insertion of foreign genes into the MVA genome was targeted precisely to the site of the naturally occurring deletion II in the MVA genome. Sequences of MVA DNA flanking the site of a 2500 bp deletion in the HindIII N fragment of the MVA genome (Altenburger, W., Suter, C. P. and Altenburger, J. (1989), J. Arch. Virol. 105, 15–27) were amplified by PCR and cloned into the multiple cloning site of plasmid pUC18. The primers for the left 600 bp DNA flank were 5'-CAG CAG <u>GGT ACC</u> CTC ATC GTA CAG GAC GTT CTC-3' (SEQ ID No: 1) and 5'-CAG CAG <u>CCC GGG</u> TAT TCG ATG ATT ATT TTT AAC AAA ATA ACA-3' (SEQ ID No: 2) (sites for restriction enzymes KpnI and SmaI are underlined). The primers for the right 550 bp DNA flank were 5'-CAG CAG <u>CTG CAG</u> GAA TCA TCC ATT CCA CTG AAT AGC-3' (SEQ ID No: 3) and 5'-CAG CAG <u>GCATGC</u> CGA CGA ACA AGG AAC TGT AGC AGA-3' (SEQ ID No: 4) (sites for restriction enzymes PstI and SphI are underlined). Between these flanks of MVA DNA inserted in pUC18, the E. coli lacZ gene under control of the vaccinia virus late promoter P11 (prepared by restriction digest from pIII LZ, Sutter, G. and Moss, B. (1992) PNAS USA 89, 10847–10851) was inserted, using the BamHI site, to generate the MVA insertion vector pUCII LZ. In the following, a 289 bp fragment containing the vaccinia virus early-late promoter P7.5 together with a SmaI site for cloning (prepared by restriction digest with EcoRI and XbaI from the plasmid vector pSC11 (Chakrabarti et al. 1985, Molecular and Cellular Biology 5, 3403–3409)) was inserted into the SmaI site of pUCII LZ to give the MVA vector pUC II LZ P7.5. To construct a vector plasmid that allows isolation of recombinant MVA viruses via transient synthesis of the reporter enzyme β-galactosidase a 330 bp DNA fragment from the 3' end of the E. coli LacZ open reading frame was amplified by PCR (primers were 5'-CAG CAG GTC GAC CCC GAC CGC CTT ACT GCC GCC-3' (SEQ ID No: 5) and 5'-GGG GGG CTG CAG ATG GTA GCG ACC GGC GCT CAG-3' (SEQ ID No: 6)) and cloned into the SalI and PstI sites of pUC II LZ P7.5 to obtain the MVA vector pUC II LZdel P7.5. Using the SmaI site, this vector plasmid can be used to insert DNA sequences encoding a foreign gene under transcriptional control of the vaccinia virus promoter P7.5 into the MVA genome. After the desired recombinant virus has been isolated by screening for expression of β-galactosidase activity further propagation of the recombinant virus leads to the self-deletion of the reengineered P11-LacZ expression cassette by homologous recombination.

For an alternative vector plasmid, pUC II sPi, instead of the P11-LacZ expression cassette and the P7.5 promoter a vaccinia specific synthetic promoter (prepared by a HindIII/PstI restriction digest from pIIIgpt-sP (Sutter et al., Vaccine, 1994, 12:1032) and blunted) was inserted between the flanks adjacent to the deletion II. Therefore the P11-LacZ expression cassette and the P7.5 promoter was deleted from the plasmid pUCII LZ P7.5 by a XhoI/Bpu1102 restriction digest, the vector fragment was blunted and ligated to the also blunted fragment carrying the synthetic promoter sP.

EXAMPLE 5

Construction of Recombinant MVA-preM-E Encoding Structural PreM and E Glycoprotein of Dengue Virus A cDNA fragment of dengue virus type 2, NGC strain comprising a signal sequence of 14 amino acids preceding preM and all amino acids of preM and E including 40 amino acid residues at the C-terminus of E was isolated by PCR from dengue virus type 2 cDNA (Gruenberg, et al., J. Gen. Virol. 69:1391–1398, 1988).

The fragment was blunted and cloned into the SmaI site of pUCII LZdel P7.5 to create pUCII LZdel P7.5-preM-E carrying the preM-E fragment under transcriptional control of the vaccinia virus early/late promoter P7.5. The fragment carrying the preM-E fragment under transcriptional control of the vaccinia virus early/late promoter P7.5 was inserted into deletion II within the MVA using homologous recombination. CEF cells infected with MVA at a multiplicity of 0.05 $TCID_{50}$ per cell were transfected with DNA of plasmid pUC II LZdel P7.5-preM-E as described previously (Sutter, et al., (1994) Vaccine 12, 1032–1040). Recombinant MVA viruses containing the preM-E sequence and transiently co-expressing the *E. coli* LacZ marker gene were selected by consecutive rounds of plaque purification in CEF cells stained with 5-bromo-4-chloro-3-indolyl β-D-galactoside (300 µg/ml). In the following, recombinant MVA viruses containing the preM-E sequence and having deleted the LacZ marker gene were isolated by three additional consecutive rounds of plaque purification screening for non-staining viral foci in CEF cells in the presence of 5-bromo-4-chloro-3-indolyl β-galactoside (300 µg/ml). Subsequently, recombinant viruses were amplified by infection of CEF monolayers.

EXAMPLE 6

Construction of Recombinant MVA-NS1 Encoding Non-structural NS1 Gycoprotein of Dengue Virus A cDNA fragment of dengue virus serotype 2, New Guinea C (NGC) strain comprising a signal sequence of 24 amino acids preceding NS1 and all NS1 residues was isolated by PCR from Dengue virus type 2 cDNA (Gruenber, et al., J. Gen. Virol. 69:1391–1398, 1988).

The fragment was blunted and cloned into the SmaI site of pUCII LZdel P7.5 to create pUCII LZdeI P7.5-NS1 carrying the NS1 fragment under transcriptional control of the vaccinia virus early/late promoter P7.5.

The fragment carrying the NS1 fragment under transcriptional control of the vaccinia virus early/late promoter P7.5 was inserted into deletion II within the MVA using homologous recombination as describe, subsequent selection for recombinant virus was performed like in example 5.

EXAMPLE 7

Construction of MVA Vector Viruses Producing Recombinant Modified Dengue Virus Glycoprotein E With its Authentic Amino Acid Leader Sequence A cDNA fragment containing codons for start and stop of translation and encoding 326 amino acids of Dengue virus type 2, New Guinea C (NGC) strain (nucleotides 768–1733, Gruenberg, et al., 1988, J. Gen. Virol. 69:1391–1398) comprising a signal sequence of 31 amino acids preceding Dengue glycoprotein E, all 295 amino acids of domain I and II of glycoprotein E, but missing 202 amino acids of domain III from the C-terminal part of glycoprotein E, was isolated by PCR from cloned cDNA of Dengue virus type 2 NGC strain (Gruenberg, et al., J. Gen. Virol. 69:1391–1398, 1988) using the oligonucleotides 5'-CAG CAG CCC GGG ATG GCA GCA ATC CTG GCA TAC ACC -3' (SEQ ID No: 7) and 5'-CAG CAG CCC GGG TCA CTG TAG TTT GTC CAT CCT CAG CCT -3' (SEQ ID No: 8) as primers.

The prepared fragment was cloned into the PmeI site of the MVA vector plasmid pUCII sP to create the plasmid pUCII sP-denET carrying the Dengue virus $E_T$-cDNA fragment under transcriptional control of a strong synthetic vaccinia virus promoter as described previously (Sutter, et al., (1994) Vaccine 12, 1032–1040). The fragment carrying the Dengue virus $E_T$-cDNA fragment under transcriptional control of a strong synthetic vaccinia virus promoter was inserted into deletion II within the MVA genome using homologous recombination. CEF cells infected with MVA at a multiplicity of 0.05 $TCID_{50}$ per cell were transfected with DNA of pUCII sP-denE$_T$ as described previously (Sutter, et al., (1994) Vaccine 12, 1032–1040).

Recombinant MVA viruses containing the Dengue virus $E_T$-cDNA were selected by consecutive rounds of plaque purification in CEF cells using Dengue glycoprotein E-specific mouse monoclonal antibodies for live immunostaining of cells expressing the desired recombinant protein. Subsequently, recombinant viruses were amplified by infection of CEF monolayers.

EXAMPLE 8

Construction of MVA Vector Viruses Producing Recombinant Modified Dengue Virus Glycoprotein E With its Authentic Amino Acid Leader Sequence A cDNA fragment containing codons for start and stop of translation and encoding 326 amino acids of Dengue virus type 2, New Guinea C (NGC) strain (nucleotides 768–1733, Gruenber, et al., J. Gen. Virol. 69:1391–1398, 1988) comprising a signal sequence of 31 amino acids preceding Dengue glycoprotein E, all 295 amino acids of domain I and II of glycoprotein E, but missing 202 amino acids of domain III from the C-terminal part of glycoprotein E, was isolated by PCR from cloned cDNA of Dengue virus type 2 NGC strain (Gruenberg, et al., J. Gen. Virol. 69:1391–1398, 1988) using the oligonucleotides 5'-CAG CAG CCC GGG ATG GCA GCA ATC CTG GCA TAC ACC -3' (SEQ ID No: 7) and 5'-CAG CAG CCC GGG TCA CTG TAG TTT GTC CAT CCT CAG CCT -3' (SEQ ID No: 8) as primers.

The prepared fragment was cloned into the SmaI site of the MVA vector plasmid pUCII LZdel P7.5 to create the plasmid pUCII LZdel P7.5-den$_{ET}$ carrying the Dengue virus $E_T$-cDNA fragment under transcriptional control of the vaccinia virus early/late promoter P7.5. The fragment carrying the $E_T$cDNA fragment under transcriptional control of the vaccinia virus early/late promoter P7.5 was inserted into deletion II within the MVA using homologous recombination. CEF cells infected with MVA at a multiplicity of 0.05 $TCID_{50}$ per cell were transfected with DNA of plasmid pUC II LZdel P7.5-denE$_T$ as described previously (Sutter, et al., (1994) Vaccine 12, 1032–1040). Recombinant MVA viruses containing the Dengue virus cDNA sequence and transiently co-expressing the *E. coli* LacZ marker gene were selected by consecutive rounds of plaque purification in CEF cells stained with 5-bromo-4-chloro-3-indolyl β-D-galactoside (300 μg/ml). In the following, recombinant MVA viruses containing the $E_T$ sequence and having deleted the LacZ marker gene were isolated by three additional consecutive rounds of plaque purification screening for non-staining viral foci in CEF cells in the presence of 5-bromo-4-chloro-3-indolyl β-D-galactoside (300 μg/ml). Subsequently, recombinant viruses were amplified by infection of CEF monolayers.

EXAMPLE 9

Construction and Characterisation of Recombinant Virus MVA T7pol

A 3.1 kb DNA fragment containing the entire gene of bacteriophage T7 RNA polymerase under control of the vaccinia virus early/late promoter P7.5 was excised with EcoRI from plasmid pTF7-3 (Fuerst, et al., 1986, P. N. A. S. USA 83, 8122–8126), modified by incubation with Klenow DNA polymerase to generate blunt ends, and cloned into a unique SmaI restriction site of pUCII LZ to make the plasmid transfer vector pUCII LZ T7pol. The plasmid pUCII LZ T7pol that directs the insertion of the foreign genes into the site of deletion II of the MVA genome was used to generate the recombinant virus MVA-T7pol.

CEF cells infected with MVA at a multiplicity of 0.05 $TCID_{50}$ per cell were transfected with DNA of plasmid pUCII LZ T7pol as described previously (Sutter, et al., (1994) Vaccine 12, 1032–1040). Recombinant MVA virus expressing the T7 RNA polymerase and co-expressing β-D-galactosidase (MVA-T7pol ) was selected by five consecutive rounds of plaque purification in CEF cells stained with 5-bromo-4-chloro-3-indolyl β-D-galactoside (300 μg/ml). Subsequently, recombinant viruses were amplified by infection of CEF monolayers, and the DNA was analyzed by PCR to confirm genetic homogeneity of the virus stock. The usefulness of MVA-T7pol recombinant viruses as expression system in comparison to the WR-T7pol recombinant virus vTF7-3 (Fuerst et a., 1986) was tested by the co-transfection of DNA of a plasmid vector that is derived from pTM1 (Moss, et al., (1990) Nature 348, 91–92) and contains (cloned into the NcoI and BamHI sites of the pTM1 multiple cloning site) the *E. coli* chloramphenicol acetyl-transferase (CAT) gene under the control of a T7 RNA polymerase promoter ($PT_7$). Transfected and infected CV-1 cells were suspended in 0.2 ml of 0.25 M Tris-HCl (pH 7.5). After three freeze-thaw cycles, the lysates were cleared by centrifugation, the protein content of the supernatants was determined, and samples containing 0.5, 0.25, 0.1 μg total protein were assayed for enzyme activity as described by Mackett, et al., (1984) J. Virol. 49, 857–864. After autoradiography, labelled spots were quantitated using the Fuji imaging analysis system.

The results demonstrate that by using the highly attenuated vaccinia vector MVA it is possible to exploit the vaccinia virus-T7 RNA polymerase system as efficiently as by using a fully replication-competent vaccinia virus recombinant.

Recombinant DNA vectors encoding heterologous antigens under transcriptional control of the T7 RNA-polymerase promoter have been constructed as known to everybody skilled in the art using commercially available T7 expression plasmids (Invitrogen) and are used in combination with the MVA-T7pol for vaccination purposes.

EXAMPLE 10

Vaccine Preparation

For the preparation of vaccines, the recombinant MVA according to the invention are converted into a physiologically acceptable form. This can be done based on the experience in the preparation of MVA vaccines used for vaccination against smallpox (as described by Stickl, H. et al. (1974) Dtsch. med. Wschr. 99, 2386–2392). Typically, about $10^6$–$10^8$ particles of the recombinant MVA are freeze-dried in 100 ml of phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilisers, etc.) suitable for parenteral administration. The glass ampoule is then sealed and can be stored, preferably at temperatures below −20° C., for several months.

For vaccination or therapy the lyophilisate can be dissolved in 0.1 to 0.5 ml of an aqueous solution, preferably physiological saline, and administered either parenterally, for example by intramuscular inoculation or locally. Vaccines or therapeutics according to the invention are preferably injected intramuscularly (Mayr, A. et al. (1978) Zbl. Bakt. Hyg., I. Abt. Orig. B 167, 375–390). The mode of administration, the dose and the number of administrations can be optimised by those skilled in the art in a known manner. It is expedient where appropriate to administer the vaccine several times over a lengthy period in order to obtain appropriate immune responses against the foreign antigen.

Many modifications and variations of this invention will be made without departing from its spirit and scope, as will become apparent to those skilled in the art. The specific embodiment described herein are offered by way of example only, and the invention is to be limited only by the terms of the appended claims.

What is claimed is:

1. A composition comprising a first and second component, wherein the first component is a vector comprising more than one DNA sequence selected from the group consisting of a DNA sequence encoding a Dengue virus serotype 1 antigen, a DNA sequence encoding a Dengue virus serotype 2 antigen, a DNA sequence encoding a Dengue virus serotype 3 antigen, or a DNA sequence encoding a Dengue Virus serotype 4 antigen and wherein the more than one DNA sequences are under the transcriptional control of a T7 RNA polymerase promoter and the second component is a recombinant Modified Vaccinia Ankara (MVA) virus comprising a DNA sequence encoding T7 RNA polymerase.

2. The composition of claim 1, wherein the vector of the first component is a plasmid.

3. The composition according to claim 1, wherein the DNA sequence encoding Dengue virus antigen is selected from the group consisting of DNA sequences encoding preM, E and NS1 antigens.

4. The composition according to claim 1, wherein the DNA sequence encoding the t7 RNA polymerase is inserted at a site of a naturally occurring deletion with the MVA genome.

5. A cell containing the composition of claim 1.

* * * * *

UNITED STATES PATENT AND TRADEMARK OFFICE
CERTIFICATE OF CORRECTION

PATENT NO. : 6,869,793 B2  
DATED : March 22, 2005  
INVENTOR(S) : Cardosa et al.

Page 1 of 1

It is certified that error appears in the above-identified patent and that said Letters Patent is hereby corrected as shown below:

<u>Title page,</u>  
Item [73], Assignee, after "(DK)" insert  
-- Universiti Malaysia Sarawak and GSF-Forschungszentrum fur Umwelt und Gesundheit GmbH. --.

Signed and Sealed this

Fourth Day of April, 2006

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 6,869,793 B2 | Page 1 of 1 |
| APPLICATION NO. | : 09/147919 | |
| DATED | : March 22, 2005 | |
| INVENTOR(S) | : Cardosa et al. | |

It is certified that error appears in the above-identified patent and that said Letters Patent is hereby corrected as shown below:

Title page,
Item [73], Assignee, after "(DK)" insert
-- Universiti Malaysia Sarawak, Sarawak, Malaysia and GSF-Forschungszentrum fur Umwelt and Gsundheit GmbH, Neuherberg, Germany --.

This certificate supersedes certificate of correction issued April 4, 2006.

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 6,869,793 B2  
APPLICATION NO. : 09/147919  
DATED : March 22, 2005  
INVENTOR(S) : Mary Jane Cardosa et al.

Page 1 of 1

It is certified that error appears in the above-identified patent and that said Letters Patent is hereby corrected as shown below:

Title Page
Item [73], Assignee, please replace "Bavarian Nordic Research Institute, Glostrup (DK)" with "Bavarian Nordic A/S, Kvistgard (DK)"

Signed and Sealed this

Tenth Day of February, 2009

JOHN DOLL  
*Acting Director of the United States Patent and Trademark Office*